US010258328B2

(12) United States Patent
Penzimer

(10) Patent No.: US 10,258,328 B2
(45) Date of Patent: Apr. 16, 2019

(54) FIXATION ASSEMBLY AND METHOD OF USE

(71) Applicant: Extremity Medical, LLC, Parsippany, NJ (US)

(72) Inventor: Raymond Penzimer, Morristown, NJ (US)

(73) Assignee: Extremity Medical, LLC, Parsippany, NJ (US)

( * ) Notice: Subject to any disclaimer, the term of this patent is extended or adjusted under 35 U.S.C. 154(b) by 726 days.

(21) Appl. No.: 14/594,953

(22) Filed: Jan. 12, 2015

(65) Prior Publication Data

US 2016/0199113 A1 Jul. 14, 2016

(51) Int. Cl.
*A61B 17/80* (2006.01)
*A61B 17/064* (2006.01)
*A61B 17/84* (2006.01)
*A61B 17/86* (2006.01)
*A61B 17/17* (2006.01)
*A61B 17/56* (2006.01)

(52) U.S. Cl.
CPC ...... *A61B 17/0642* (2013.01); *A61B 17/1775* (2016.11); *A61B 17/1782* (2016.11); *A61B 17/846* (2013.01); *A61B 17/8605* (2013.01); *A61B 17/864* (2013.01); *A61B 2017/564* (2013.01)

(58) Field of Classification Search
CPC .................................................. A61B 17/809
See application file for complete search history.

(56) References Cited

U.S. PATENT DOCUMENTS

| 4,011,863 A | 3/1977 | Zickel |
| 4,381,770 A | 5/1983 | Neufeld |

(Continued)

FOREIGN PATENT DOCUMENTS

| FR | 2676353 A1 | 11/1992 |
| WO | WO9402073 A1 | 2/1994 |

*Primary Examiner* — Nicholas W Woodall
(74) *Attorney, Agent, or Firm* — Kelley Drye & Warren LLP

(57) ABSTRACT

A fixation assembly for bone fixation and a method for joining bones or bone fragments of a single bone and translating uniform compression to the bones. The fixation assembly comprises a post member coupled to a screw member. The post member comprises a head portion connected to an anchoring portion, wherein the head portion is offset from the anchoring portion by a first angle. The head portion may comprise a curved body annularly extending from a first end to a second end, wherein the first end is separated from the second end by a slot, and wherein the curved body defines a tapered annular bore therein. The anchoring portion comprises a first leg extending from the first end of the curved body and a second leg extending from the second end of the curved body. The screw member comprises a tapered bulbous portion connected to a threaded elongated portion. The screw member is coupled to the post member by advancing the elongated portion of the screw member through the tapered bore of the post member until the tapered bulbous portion of the screw member abuts the tapered bore of the post member thereby creating an interference fit. The first angle of the post member determines the angle of fixation of the post member with respect to the screw member.

40 Claims, 12 Drawing Sheets

(56) References Cited

U.S. PATENT DOCUMENTS

| | | |
|---|---|---|
| 4,503,847 A | 3/1985 | Mouradian |
| 4,838,254 A | 6/1989 | Gauthier |
| 4,915,092 A | 4/1990 | Firica et al. |
| 4,936,844 A * | 6/1990 | Chandler ............ A61B 17/0642 606/282 |
| 5,013,314 A | 5/1991 | Firica et al. |
| 5,662,655 A | 9/1997 | Laboureau et al. |
| 5,709,682 A | 1/1998 | Medoff |
| 5,810,822 A | 9/1998 | Mortier |
| 5,941,878 A | 8/1999 | Medoff |
| 6,168,596 B1 | 1/2001 | Wellisz et al. |
| 6,203,545 B1 | 3/2001 | Stoffella |
| 6,248,109 B1 | 6/2001 | Stoffella |
| 6,325,805 B1 | 12/2001 | Ogilvie et al. |
| 6,379,359 B1 | 4/2002 | Dahners |
| 6,511,482 B1 | 1/2003 | Wellisz et al. |
| 6,527,775 B1 | 3/2003 | Warburton |
| 6,689,136 B2 | 2/2004 | Stoffella |
| 7,037,308 B2 | 5/2006 | Medoff |
| 7,160,302 B2 | 1/2007 | Warburton |
| 7,341,591 B2 | 3/2008 | Grinberg |
| 7,588,577 B2 | 9/2009 | Fencl et al. |
| 7,678,113 B2 | 3/2010 | Melkent |
| 7,713,271 B2 | 5/2010 | Warburton |
| 7,811,286 B2 | 10/2010 | Medoff |
| 7,942,877 B2 | 5/2011 | Medoff |
| 8,034,056 B2 | 10/2011 | Fencl et al. |
| 8,092,453 B2 | 1/2012 | Warburton |
| 8,100,910 B2 | 1/2012 | Warburton |
| 8,109,980 B2 | 2/2012 | Melkent |
| 8,287,577 B2 | 10/2012 | Berberich |
| 8,343,152 B2 | 1/2013 | Gonzalez-Hernandez |
| 8,470,007 B2 | 6/2013 | Melkant |
| 2004/0111090 A1 | 6/2004 | Dahners |
| 2006/0015101 A1 | 1/2006 | Warburton et al. |
| 2006/0200143 A1 | 9/2006 | Warburton |
| 2006/0200144 A1 | 9/2006 | Warburton |
| 2008/0091203 A1 | 4/2008 | Warburton et al. |
| 2009/0157077 A1 | 6/2009 | Larsen et al. |
| 2009/0157079 A1 | 6/2009 | Warburton et al. |
| 2009/0157080 A1 | 6/2009 | Warburton |
| 2009/0292292 A1 | 11/2009 | Fencl et al. |
| 2011/0009912 A1 | 1/2011 | Gonzalez-Hernandez et al. |
| 2012/0150240 A1 | 6/2012 | Medoff |
| 2012/0265301 A1 * | 10/2012 | Demers ............... A61B 17/8095 623/16.11 |
| 2013/0123864 A1 | 5/2013 | Gonzalez-Hernandez |
| 2013/0238035 A1 | 9/2013 | Medoff |

* cited by examiner

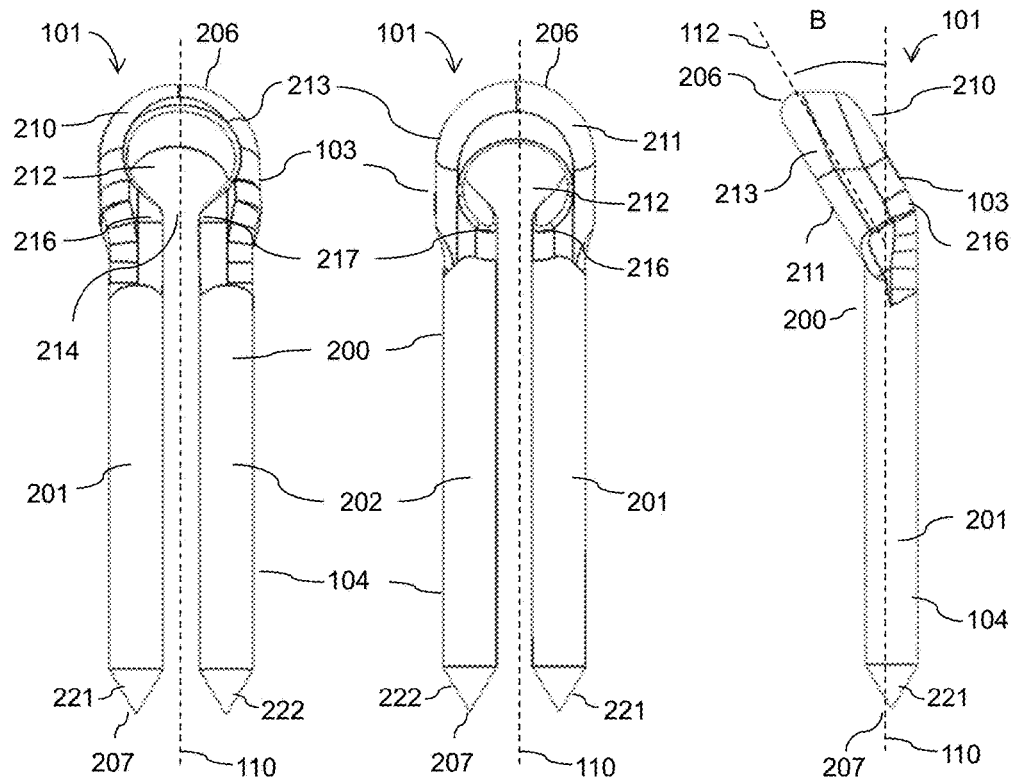
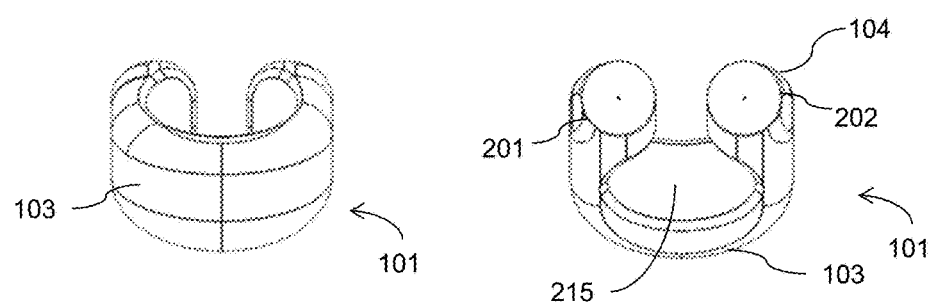

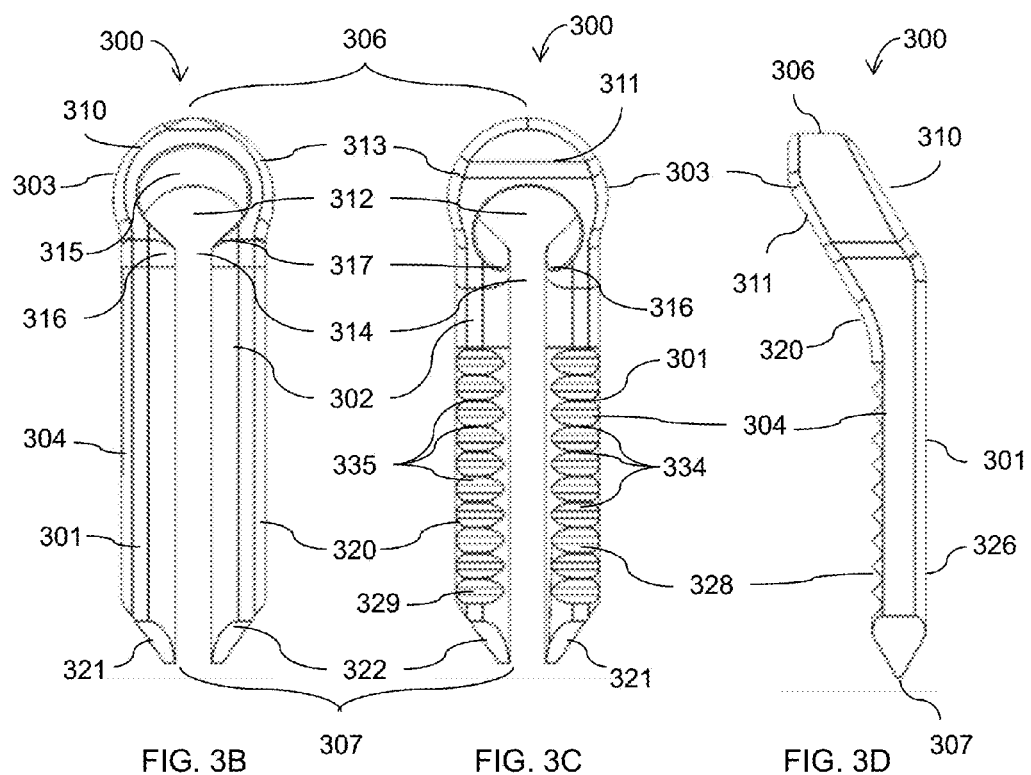
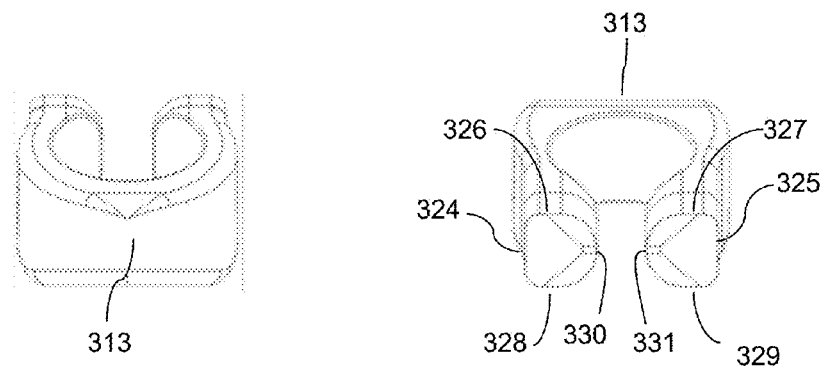
FIG. 3E
FIG. 3F

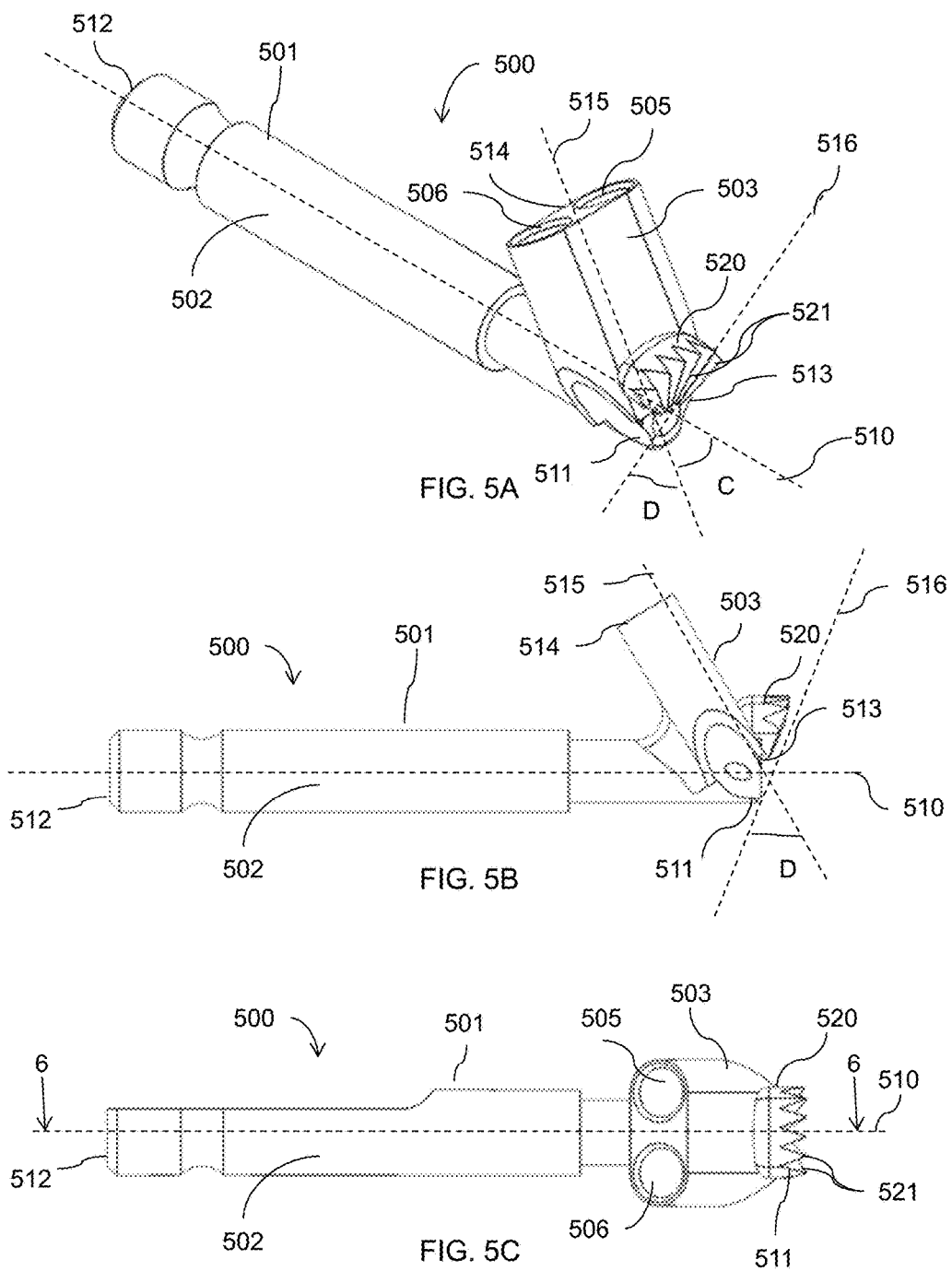

FIXATION ASSEMBLY AND METHOD OF USE

FIELD OF THE INVENTION

This invention relates to the field of implant devices, and more particularly, to a fixation assembly for joining bones by applying uniform compression through multi-point fixation.

BACKGROUND OF THE INVENTION

Implant devices, such as intramedullary nails, plates, rods, screws, Kirschner wires (K-wires), and screw-and-washer assemblies are often used to repair or reconstruct bones and joints affected by trauma, degeneration, deformity, fractures, and disease, such as Charcot arthropathy caused by diabetes in some patients, Hallux Valgus deformities, failed Keller Bunionectomies, Rheumatoid Arthritis, injuries, and severe deformities. Infections and wound complications are a major concern in the aforementioned procedures. Wound closure is technically demanding for the surgeon, and devices that add surface prominence, such as plates or exposed screws, add to the difficulty by requiring greater tissue tension during incision reapproximation. This increases the risk of postoperative wound infections and dehiscence that may ultimately result in limb amputation.

Various implants have been utilized for surgical treatment of these bones and joints, including bone screws. Implants have also been utilized to treat severe deformities in the metatarsal and phalangeal bones, including multiple screws and plates. These multiple screws and plate implants have been commonly used in a first metatarsal-phalangeal fusion procedure to fuse the first metatarsal to the first phalangeal bone in hallux valgus deformities, failed Keller bunionectomies, rheumatoid arthritis, and other types of severe deformities in the metatarsal and phalange bones. While these devices allow fixation and promote fusion, they do not deliver restoration of the arch in a Charcot foot, they are not effective in metatarsal-phalangeal (MTP) fusion procedures, nor do they deliver uniform compression for various predetermined angles of compression.

Particularly, screw implants in MTP procedures are ineffective in delivering sufficient compression to the bones in the foot, preventing screw head break out, or delivering effective bending resistance. Moreover, hard to control dorsiflexion and valgus angles as well as skin irritation from proximity to the skin prevents these screw implants from being readily utilized for surgical treatment. Yet further, plate implants used with bone screws too have the same drawbacks as fixed varus and valgus angles, lack of direct compression across the MTP joint, and skin irritations from proximity to the skin reduce the effectiveness of these implants.

Still further, use of K-wires, screws, screw-and-washer assemblies, and plates for the reduction and internal fixation of arthrodesis, osteotomy, intra-articular and extra-articular fractures, and non-unions of bones and joints of the hand, foot, arm, leg and various other body parts are ineffective in delivering the strength necessary to maintain sufficient reduction and/or fixation of the fractured bone, maximizing cortical bone contact, retaining bones in most anatomically correct position, preventing screw head break out, minimizing the size of the incision(s) necessary to install the hardware, minimizing soft tissue and tendon disruption and/or displacement, stabilizing fixation of the fracture, easing mobility for the patient, and eliminating hardware profiles.

There is therefore a need for a fixation assembly and method of use that overcomes some or all of the previously delineated drawbacks of prior fixation assemblies.

SUMMARY OF THE INVENTION

An object of the invention is to overcome the drawbacks of previous inventions.

Another object of the invention is to provide a novel and useful fixation assembly that may be utilized to treat bones in a human body.

Another object of the invention is to provide a system for compressing bones using a fixation assembly.

Another object of the invention is to fuse bones through the use of an intraosseous assembly.

Another object of the invention is to provide a novel fixation assembly that is securely assembled by securing a screw member to a post member via a tapered connection or engagement.

Another object of the invention is to provide a fixed acute angle fixation assembly for bone fixation.

Another object of the invention is to provide a fixation assembly that provides sufficient strength, delivers a highly stable fixation, and maintains reduction of a fractured bone.

Another object of the invention is to provide a fixation assembly that maximizes cortical bone contact.

Another object of the invention is to provide a fixation assembly that fixates to the subchondral bone and/or the cortical bone.

Another object of the invention is to provide a fixation assembly that retains and realigns bones in anatomically correct positions.

Another object of the invention is to provide a fixation assembly that reduces and/or eliminates unnecessary hardware.

Another object of the invention is to provide a fixation assembly that minimizes the size of the incision(s) necessary to install the fixation assembly.

Another object of the invention is to provide a fixation assembly that minimizes soft tissue and tendon disruption and/or displacement.

Another object of the invention is to provide a fixation assembly that allows for early post procedure mobilization of the patient.

Another object of the invention is to provide a fixation assembly that reduces and/or eliminates hardware profiles.

Another object of the invention is to provide a method for the reduction and fixation of arthrodesis, osteotomy, intra-articular and extra-articular fractures and non-unions of bones and joints of the hand, foot, arm, leg and various other body parts.

In one embodiment of the invention, a fixation assembly for bone fixation is provided comprising a post member coupled to a screw member. The post member comprises a head portion connected to an anchoring portion, wherein the head portion is offset from the anchoring portion by a first angle. The head portion may comprise a curved body annularly extending from a first end to a second end, wherein the first end is separated from the second end by a slot, and wherein the curved body defines a tapered annular bore therein. The anchoring portion comprises a first leg extending from the first end of the curved body and a second leg extending from the second end of the curved body. The screw member comprises a tapered bulbous portion connected to a threaded elongated portion. The screw member is coupled to the post member by advancing the elongated portion of the screw member through the tapered bore of the post member until the tapered bulbous portion of the screw member abuts the tapered bore of the post member thereby creating an interference fit. The first angle of the post member determines the angle of fixation of the post member with respect to the screw member. The fixation assembly of the present invention translates uniform compression to first and second bone segments (i.e., a first bone and a second bone, or first and second bone fragments of a single bone).

Broadly, the methods of the invention for joining and compressing a first bone segment to a second bone segment comprises: creating a first hole in the first bone segment and a second hole in the second bone segment along a first longitudinal axis; creating a depression below the cortex of the first bone segment by removing bone material from the first bone segment; creating third and fourth parallel holes in the first bone segment along a second longitudinal axis; advancing the first and second legs of the post member into the third and fourth parallel holes in the first bone segment; pressing the head portion of the post member into the depression in the first bone segment; and advancing the screw member through the bore of the post member and into the first hole in the first bone segment and the second hole in the second bone segment until the bulbous portion of the screw member abuts the bore of the post member.

Instruments are also disclosed for use in practicing the invention. Numerous variations may be practiced in the preferred embodiment.

BRIEF DESCRIPTION OF THE DRAWINGS

A further understanding of the invention can be obtained by reference to a preferred embodiment set forth in the illustrations of the accompanying drawings. Although the illustrated embodiment is merely exemplary of systems and methods for carrying out the invention, both the organization and method of operation of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the invention, reference is now made to the following drawings in which:

FIG. 2B is a front view of the post member shown in FIG. 2A according to an embodiment of the invention;

FIG. 2C is a rear view of the post member shown in FIG. 2A according to an embodiment of the invention;

FIG. 2D is a side view of the post member shown in FIG. 2A according to an embodiment of the invention;

FIG. 2E is a top view of the post member shown in FIG. 2A according to an embodiment of the invention;

FIG. 2F is a bottom view of the post member shown in FIG. 2A according to an embodiment of the invention;

FIG. 3B is a front view of the post member shown in FIG. 3A according to the alternate embodiment of the invention;

FIG. 3C is a rear view of the post member shown in FIG. 3A according to the alternate embodiment of the invention;

FIG. 3D is a side view of the post member shown in FIG. 3A according to the alternate embodiment of the invention;

FIG. 3E is a top view of the post member shown in FIG. 3A according to the alternate embodiment of the invention;

FIG. 3F is a bottom view of the post member shown in FIG. 3A according to the alternate embodiment of the invention;

FIG. 5A is a perspective view of an instrument used to couple the fixation assembly shown in FIG. 1 to the bones according to an embodiment of the invention;

FIG. 5B is a side view of the instrument shown in FIG. 5A according to an embodiment of the invention;

FIG. 5C is a top view of the instrument shown in FIG. 5A according to an embodiment of the invention;

DETAILED DESCRIPTION OF THE INVENTION

The invention may be understood more readily by reference to the following detailed description of preferred embodiment of the invention. However, techniques, systems, and operating structures in accordance with the invention may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein, which define the scope of the invention. It must be noted that, as used in the specification and the appended claims, the singular forms "a", "an", and "the" include plural referents unless the context clearly indicates otherwise.

Figure 1:
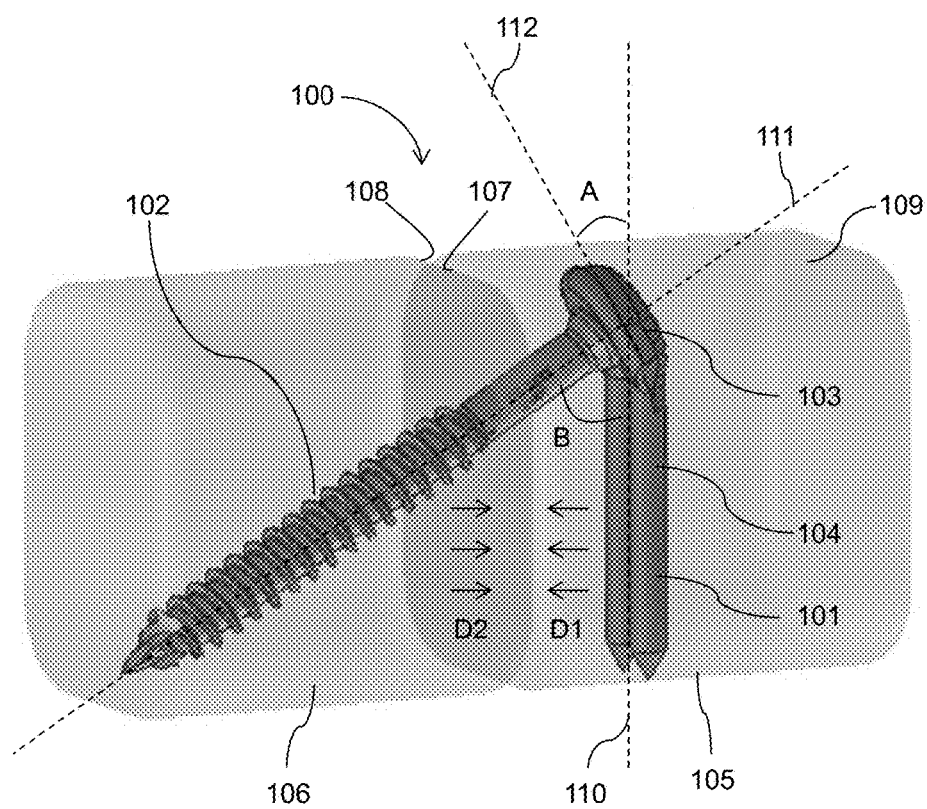
FIG. 1 is a perspective view of a fixation assembly according to an embodiment of the invention.

Referring now to FIG. 1, there is shown a fixation assembly 100 which is made in accordance with the teachings of the preferred embodiment of the invention. As shown, the fixation assembly 100 includes a screw member 102 adapted to be locked to a post member 101. Fixation assembly 100 is used to translate intraosseous and uniform compression to bone segments (i.e., a plurality of bones or a plurality of bone fragments of a single bone) for treating and fusing deteriorated, damaged, or fractured bones in the human body. In particular, fixation assembly 100 may be used for the reduction and internal fixation of arthrodeses, osteotomies, intra- and extrarticular fractures and nonunions of the small bones and joints of the foot and ankle. Fixation assembly 100 preferably delivers the strength necessary to maintain sufficient reduction and/or fixation of a fractured bone, maximizes cortical bone contact, retains bones in an anatomically correct position, prevents screw head break out, minimizes the size of the incision(s) necessary to install the hardware, minimizes soft tissue and tendon disruption and/or displacement, stabilizes fixation of the fracture, eases mobility for the patient, provides early post-operation mobilization of the fracture bone, and reduces and/or eliminates hardware profiles. Moreover, fixation assembly 100 generally provides a more stable and rigid fixation than the prior art because it is fixed to the strongest bone near the fracture and because it redistributes the force normally placed on the head of a screw along the assembly.

For example, fixation assembly 100 may be used to join a first bone 105 having a proximal end 107 and side surface 109 to a second bone 106 having a distal end 108, and specifically, to join the proximal end 107 of first bone 105 with distal end 108 of second bone 106. The fixation assembly 100 can be used to joint any bones of the hand and the foot, as well as for internal fixation of any other bones in the human body, including, but not limited to, the talus and navicular bones in the talonavicular joint, the calcaneus and cuboid bones in the calcaneocuboid joint, the metatarsal and cuneiform bones in the metatarsocuneiform joints, the tibia and talus bones in the tibiotalar joint, metatarsal osteotomies, as well as the metatarsals and the phalanges. The fixation assembly 100 may be further used to joint bone fragments of a single bone to treat bone fractures. It should be appreciated that screw member 102 and post member 101 of fixation assembly 100 may be provided at several sizes, lengths or widths, for the internal fixation of a variety of bone sizes in the human body.

Post member 101 comprises an anchoring portion 104 aligned along longitudinal axis 110 extending along the length of post member 101 for anchoring post member 101 in bone 105. Post member 101 further comprises a head portion 103 aligned along longitudinal axis 112 and offset from the anchoring portion 104 and longitudinal axis 110 at an angle A. Angle A determines the angle of fixation of post member 101 with respect to the screw member 102. Angle A is provided at various angles depending on the bone fragments that are being compressed. Angle A may be any angle less than 90 degrees and is preferably in the range of about 30 degrees to about 75 degrees. Screw member 102 is aligned along longitudinal axis 111 and is fixed to the post member 101 at angle B. Angle B may be any angle less than 90 degrees and is preferably in the range of about 15 degrees to about 60 degrees. Angle B causes the fixation assembly 100 to "hook" into bones 105 and 106 and translate uniform compression applied to the bones through multi-point fixation. In particular, fixation assembly 100 distributes compressive forces across a wide surface area providing orthogonal multi-plane fixation and bicortical cross screw fixation to bones. In a locked position, screw member 102 compresses bones 105 and 106, while the post member 101 acts as an intraosseous bicortical anchor, which lags bones 105 and 106 together in a parallel fashion in directions D1 and D2. Beneficially, fixation assembly 100 maintains compression even if the cortical bridge of the bone is compromised.

It should also be appreciated that the fixation assembly 100 is implanted through a minimal incision and is provided to be substantially within the bone (i.e., intraosseous), thereby reducing the disruption to the plantar tissues while at the same time minimizing the tension on the skin. This allows for improved wound closure, reduced operating room time, reduction in the number of incisions required, and reduction in the total length of incisions. Fixation assembly 100 may also be utilized with graft material (i.e., autograft, allograft or other biologic agent). Furthermore, it should be appreciated that a plurality of fixation assemblies, such as fixation assembly 100, may be inserted into any of the bones of the body, such as but not limited to, radial, humerus, tibia, and femur, in order to fixate fractures, without limiting the scope of the invention. For example, the orientation of fixation assembly 100 and method of use may be utilized to fixate a distal radius fracture by rigidly fixating two fixation assemblies 100 to the subchondral bone and/or cortical bone and applying acute angle compression to the fracture. This orientation and method of use maintains reduction of the fracture by realigning the bone to its natural anatomical position, which allows for quicker healing time and earlier mobilization of the patient.

Figure 2A:
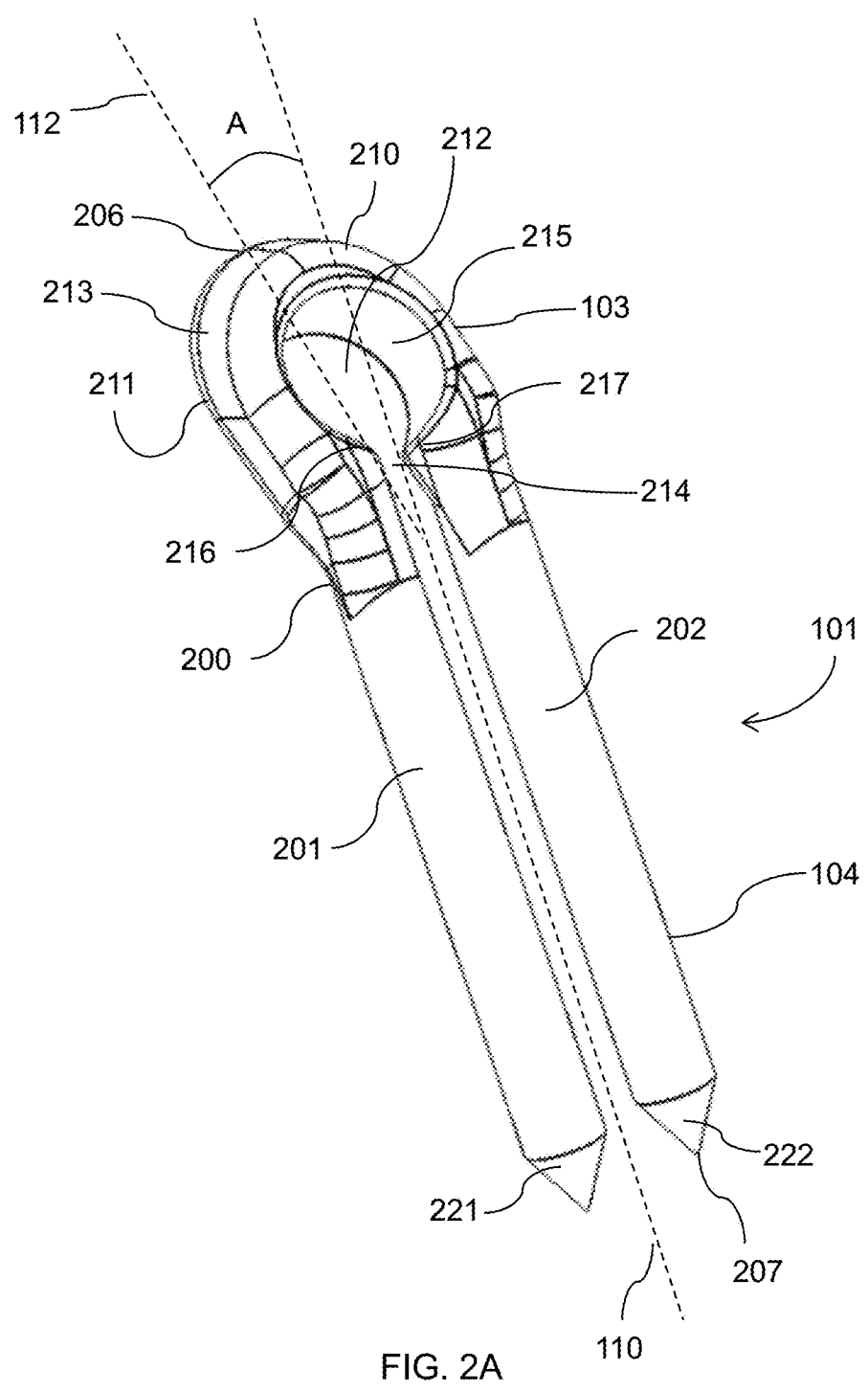
FIG. 2A is a front perspective view of a post member of the fixation assembly shown in FIG. 1 according to an embodiment of the invention.

Post member 101 of fixation assembly 100 is shown in greater detail in FIGS. 2A-2F, where FIG. 2A is a front perspective view of the post member 101, FIG. 2B is a front view thereof, FIG. 2C is a rear view thereof, FIG. 2D is a side view thereof, FIG. 2E is a top view thereof, and FIG. 2F is a bottom view thereof. Post member 101 preferably comprises unitary elongated body 200 extending from a first end 206 to a second end 207. Post member 101 is aligned along longitudinal axis 110, which is longitudinally coextensive the length of post member 101. Post member 101 may be made of materials known in the art, including titanium, titanium alloy, stainless steel, cobalt chrome, PEEK, and resorbable polyactic acid (PLA). Also, post member 101 may be coated with an osteoconductive material, such as, for example, plasma spray or other similar types of porous materials, that are capable of supporting or encouraging bone ingrowth into the material. It should be appreciated that the length of the post member 101 may be selected of varying lengths to allow a surgeon to fuse different joints in the human body.

Post member 101 comprises a head portion 103 at its first end 206 fixed to an anchoring portion 104 at its second end 207. Head portion 103 is aligned along longitudinally axis 112 and is offset from the anchoring portion 104 and longitudinal axis 110 by angle B. Angle A determines the angle for fixation of post member 101 with respect to the screw member 102 at angle B (shown in FIG. 1). Angle A is provided at various angles depending on the bone fragments that are being compressed. Angle A may be any angle less than 90 degrees and is preferably in the range of about 30 degrees to about 75 degrees. Head portion 103 preferably comprises a curved body 213. However, head portion 103 may comprise any other shape including a rectangular shape or a non-uniform shape. Curved body 213 annularly extends from a first end 216 to a second end 217, separated by a slot 214. Curved body 213 has an annular bore 212, which traverses head portion 103 through its width and extends from a front face 210 to a rear face 211 of head portion 103 along longitudinal axis 111 (shown in FIG. 1). Bore 212 annularly extends from a first end 216 to a second end 217, wherein the first end 216 is separated from the second end 217 by slot 214. Bore 212 is sized and shaped to receive a head of screw member 102 as is shown in FIG. 1. Bore 212 preferably comprises an inner wall 215 having a taper. Bore 212 tapers from front face 210 to rear face 211—i.e., bore 212 has a diameter that decreases from front face 210 to rear face 211. In a preferred embodiment, bore 212 comprises a Morse taper.

Anchoring portion 104 is adapted to be fixed transversely to a bone or a bone fragment as will be later described. Anchoring portion 104 comprises a first leg 201 and a second leg 202 extending along longitudinal axis 110. First leg 201 extends from the first end 216 of curved body 213 to second end 207 of post member 101 and second leg 202 extends from the second end 217 of curved body 213 to second end 207 of post member 101. First and second legs 201 and 202 are preferably substantially parallel and substantially cylindrical in shape. First and second legs 201 and 202 may comprise other shapes. For example, first and second legs 201 and 202 may comprise a rectangular cross-section, or a semi-circular cross-section as shown in FIGS. 3A-3F. Each of the first and second legs 201 and 202 preferably has a smooth exterior surface and comprises a substantially uniform diameter. Alternatively, first and second legs 201 and 202 may comprise a taper. First and second legs 201 and 202 of the post member 101 create a wide profile across first bone 105 because the first and second legs 201 and 202 are offset with respect to one another. The wide profile assists in providing a better-secured anchor. First and second legs 201 and 202 preferably terminate at first and second tips 221 and 222, respectively. Each of the first and second tips 221 and 222 may comprise a conical shape terminating at a point for ease of insertion of legs 201 and 202 into the bone. First and second tips 221 and 222 may comprise other shapes, as shown for example in FIGS. 3A-3F.

Figure 3A:
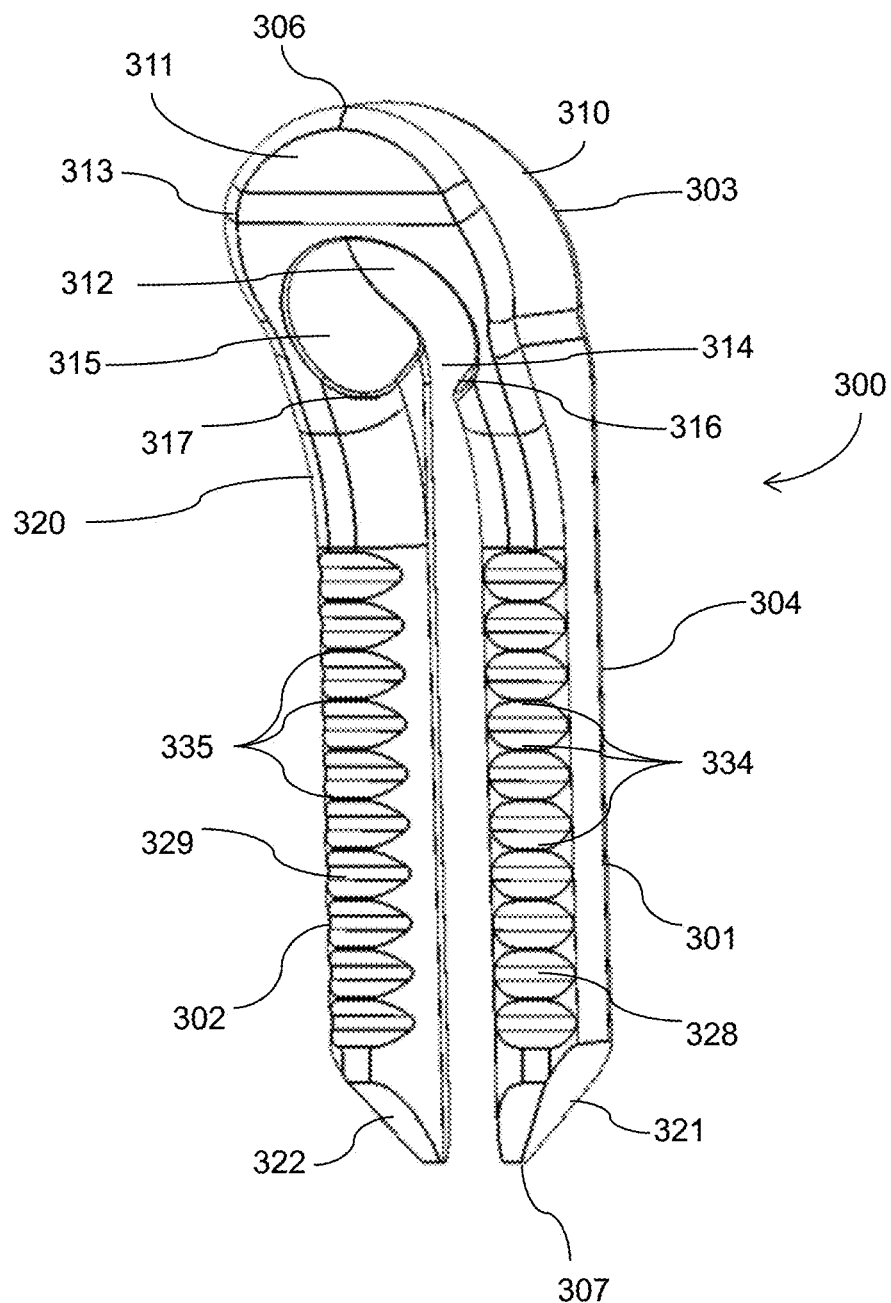
FIG. 3A is a perspective rear view of a post member of the fixation assembly shown in FIG. 1 according to an alternate embodiment of the invention.

FIGS. 3A-3F illustrate an alternative embodiment of post member 300, where FIG. 3A is a perspective rear view of the post member 300, FIG. 3B is a front view thereof, FIG. 3C is a rear view thereof, FIG. 3D is a side view thereof, FIG. 3E is a top view thereof, and FIG. 3F is a bottom view thereof. Post member 300 preferably comprises unitary elongated body 320 extending from a first end 306 to a second end 307. Post member 300 comprises a head portion 303 at its first end 306 fixed to an anchoring portion 304 at its second end 307.

Head portion 303 comprises a curved body 313 annularly extending from a first end 316 to a second end 317, separated by a slot 314. Curved body 313 has an annular bore 312, which traverses head portion 303 through its width and extends from the front face 310 to the rear face 311 of head portion 303. Bore 312 is sized and shaped to receive a head of screw member 102 as is shown in FIG. 1. Bore 312 preferably comprises an inner wall 315 having a taper, which tapers from front face 310 to rear face 311 (i.e., bore 312 has a diameter that decreases from front face 310 to rear face 311). In a preferred embodiment, bore 312 comprises a Morse taper.

Anchoring portion 304 is adapted to be fixed transversely to a bone or a bone fragment as will be later described. Anchoring portion 304 comprises substantially parallel first and second legs 301 and 302. First leg 301 extends from the first end 316 of curved body 313 to second end 307 of post member 300 and second leg 302 extends from the second end 317 of curved body 313 to second end 307 of post member 300. First and second legs 301 and 302 comprise a semi-circular cross-section as shown in FIG. 3F formed by partially-flat front-facing surfaces 326 and 327, oppositely disposed partially-flat rear-facing surfaces 328 and 329, flat outer-facing surfaces 324 and 325, and curved inner-facing surfaces 330 and 331. First and second legs 301 and 302 may comprise a plurality of barbs 334 and 335 extending transversely from the partially-flat rear-facing surfaces 328 and 329. Alternatively, the plurality of barbs 334 and 335 may be disposed on partially-flat front-facing surfaces 326 and 327, oppositely disposed flat outer-facing surfaces 324 and 325, curved inner-facing surfaces 330 and 331, or any combinations thereof. In addition, the plurality of barbs 334 and 335 may be disposed around the entire circumference of first and second legs 301 and 302. The plurality of barbs 334 and 335 are used to buttress legs 301 and 302 against the bone. First and second legs 301 and 302 preferably terminate at first and second tips 321 and 322, respectively. Each of the first and second tips 321 and 322 may taper from oppositely disposed flat outer facing surfaces 324 and 325 to curved inner facing surfaces 330 and 331, terminating at a point for ease of insertion of legs 301 and 302 into the bone.

Figure 4:
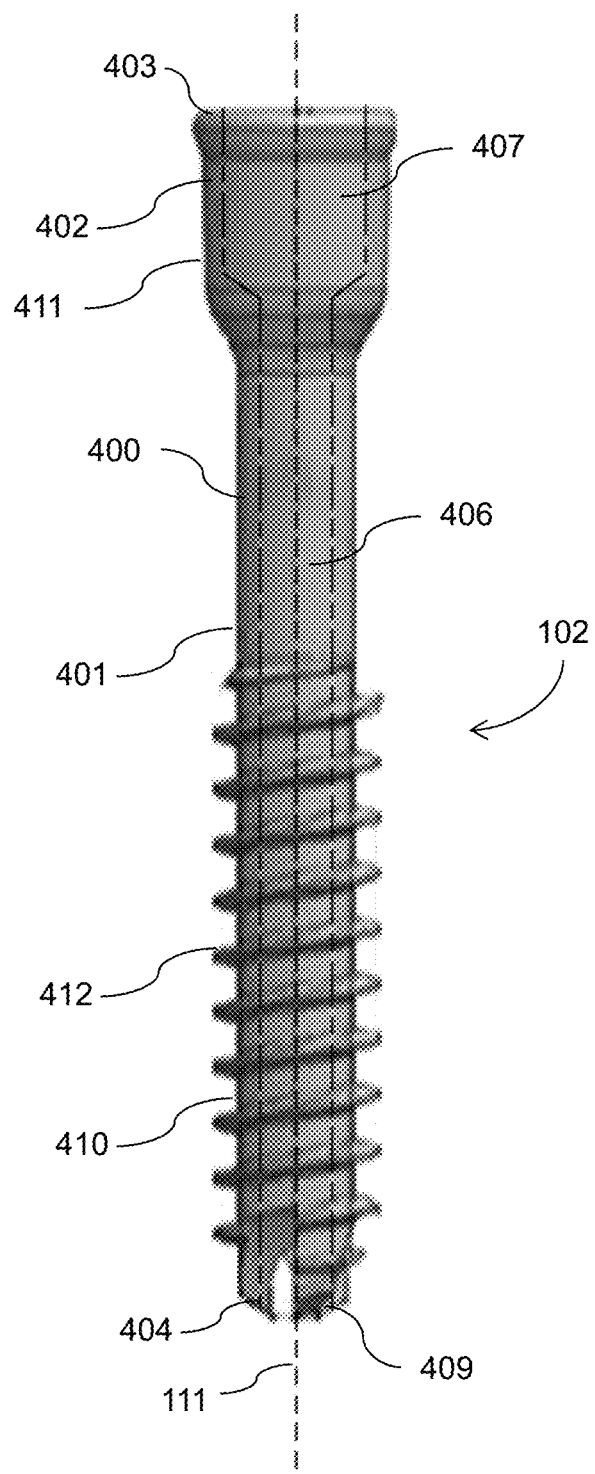
FIG. 4 is a front view of a screw member of fixation assembly shown in FIG. 1 according to an embodiment of the invention.

As shown in FIG. 4, screw member 102 comprises a unitary elongated body 400 extending from a first end 403 to a second end 404 along longitudinal axis 111. Screw member 102 may be made of materials known in the art, including titanium, titanium alloy, stainless steel, cobalt chrome, PEEK, and resorbable polyactic acid (PLA). Also, screw member 102 may be coated with an osteoconductive material, such as, for example, plasma spray or other similar types of porous materials, that are capable of supporting or encouraging bone ingrowth into the material. It should be appreciated that the length of the screw member 102 may be selected of varying lengths to allow a surgeon to fuse different joints in the human body.

Screw member 102 comprises an elongated portion 401 connected to a bulbous portion 402. The elongated portion 401 is substantially cylindrical in shape with a substantially uniform diameter. However, elongated portion 401 may be tapered from the bulbous portion 402 to the second end 404 of the screw member 102. Elongated portion 401 preferably comprises threads 412, such as helical threads, which are circumferentially disposed on the exterior surface 410 of the elongated portion 401. It should be understood that any commonly used threads for engaging and coupling may be used without limiting the scope of the invention. Elongated portion 401 may also be provided with a self-tapping leading edge 409 to provide elongated portion 401 with the ability to remove bone material during insertion of screw member 102 into bone.

Bulbous portion 402 preferably comprises a taper, such as a Morse taper, on its outer surface 411 with a diameter that decreases from first end 403 of the screw member 102 to the elongated portion 401. The taper of bulbous portion 402 allows for a locked interference fit with tapered bore 212 (shown in FIGS. 2A-2F) when tapered bulbous portion 402 resides within tapered bore 212, as shown in FIG. 1.

Moreover, bulbous portion 402 is substantially cylindrical in shape and has an aperture 407 aligned along axis 111 traversing the longitudinal length of bulbous portion 403. Aperture 407 is provided to receive an instrument (not shown) for applying torque to screw member 102. Aperture 407 may comprise any shape known in the art, including, a hexagonal-shaped aperture, a star-shaped aperture, a square-shaped aperture, or any other shaped aperture may be utilized without departing from the scope of the invention.

Screw member 102 is preferably cannulated along its longitudinal length having a bore 406 that traverses the screw member 102 along longitudinal axis 111 and extending from the first end 403 to the second end 404. Bore 406 is provided to interact with a guide wire or a Kirschner wire (K-wire) by receiving the K-wire within the bore 406 to help guide and position the screw member 102 into the bone as will be later described. Preferably, the diameter of bore 406 is constant throughout the length of the screw member 102. Different diameters and K-wire sizes may be used depending on the diameter of the bones that are being joined and the surgeon's preferences. Illustratively, the diameter of the K-wire is in the range of approximately 0.7 to 4.0 millimeters (mm), and more preferably approximately 0.9 to 1.6 mm. In another embodiment, screw member 102 may be provided without a bore 406 (i.e., the screw member 102 may be solid).

Figure 5D:
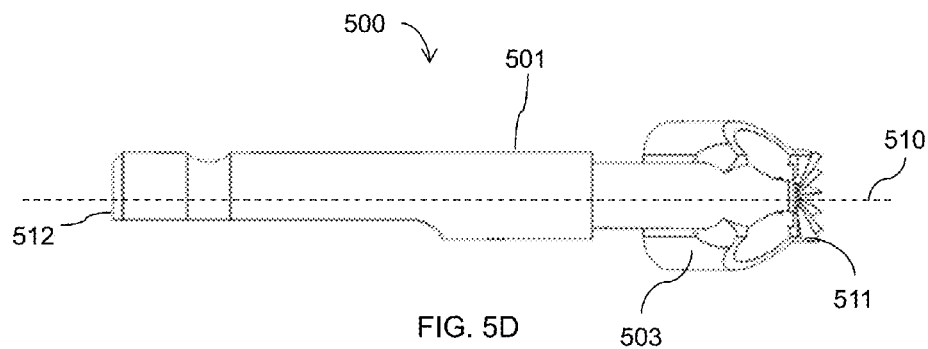
FIG. 5D is a bottom view of the instrument shown in FIG. 5A according to an embodiment of the invention.
Figure 5E:
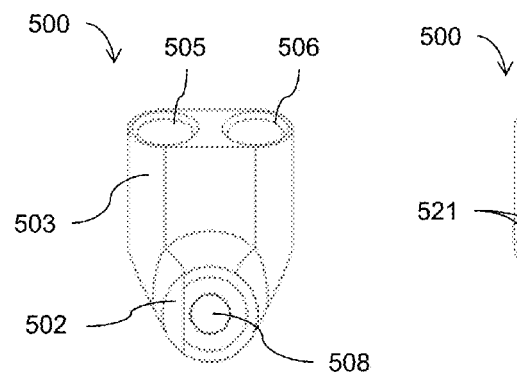
FIG. 5E is a rear view of the instrument shown in FIG. 5A according to an embodiment of the invention.
Figure 5F:
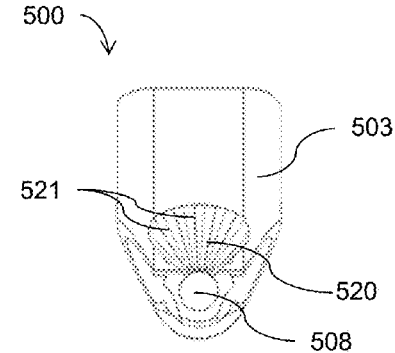
FIG. 5F is a front view of the instrument shown in FIG. 5A according to an embodiment of the invention.
Figure 6:
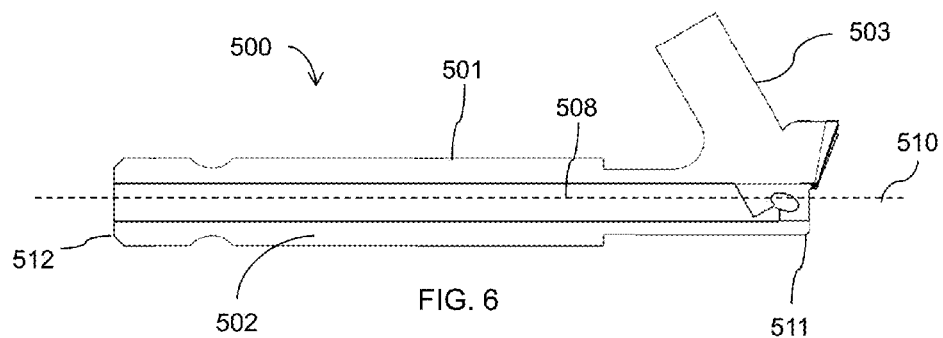
FIG. 6 is a cross-sectional view of the instrument taken along line 6-6 in FIG. 5C.
Figure 7:
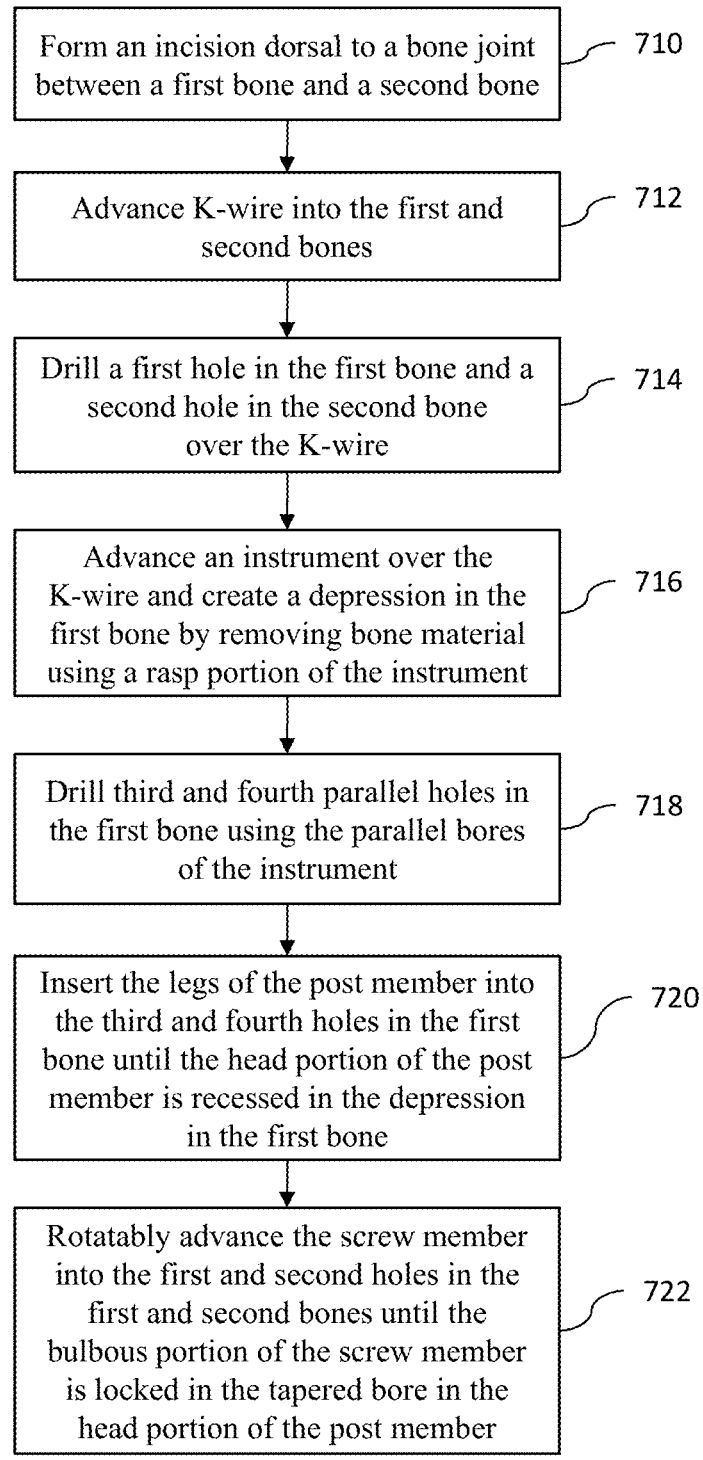
FIG. 7 is a flow chart depicting illustrative steps of a method of coupling the fixation assembly shown in FIG. 1 to bones according to an embodiment of the invention.

FIGS. 5A-5F illustrate a preferred embodiment of an instrument 500 used to couple the fixation assembly 100 to the bones. FIG. 5A illustrates the perspective side view of the instrument, FIG. 5B illustrates a side view thereof, and FIG. 5C illustrates the top view thereof, FIG. 5D illustrates the bottom view thereof, FIG. 5E illustrates the rear view thereof, and FIG. 5F illustrates the front view thereof. FIG. 6 illustrate the cross-section of the instrument taken along line 6-6 in FIG. 5C. Instrument 500 comprises a unitary elongated body 501. Elongated body 501 includes a handle portion 502 extending from a first end 511 to a second end 512 and aligned with its length along longitudinal axis 510. Handle portion 501 may be ribbed (not shown) or may comprise friction resistant material to assist the surgeon to manually apply torque to the instrument 500. Alternatively, or in addition, handle portion 501 may be sized to receive a torque transmitting tool (not show).

Elongated body 501 further comprises a head portion 503 coupled to the handle portion 502. Head portion 503 extends from a first end 513 to a second end 514 and is aligned with its length along longitudinal axis 515. Head portion 503 and handle portion 501 are coupled at their corresponding first ends 511 and 513. Head portion 503 and thereby longitudinal axis 515 is offset from the handle portion 502 and thereby offset from the longitudinal axis 510 by angle C. Angle C may be any angle less than 90 degrees and preferably it is substantially equivalent to angle B. As such, angle C is preferably in the range of about 15 degrees to about 60 degrees. Head portion 503 preferably comprises an oval cross-section transverse to longitudinal axis 515. Head portion 503 further comprises a pair of parallel bores 505 and 506 that traverse head portion 503 along longitudinal axis 515 from the first end 513 to the second end 514. In a preferred embodiment, bores 505 and 506 are sized, shaped, and spaced-apart to correspond to first and second legs 201 and 202 of post member 101. Preferably bores 505 and 506 are substantially cylindrical in shape with a substantially uniform diameter. Head portion 503 further comprises a rasp portion 520 extending transversely from its front end 513. Rasp portion 520 comprises a plurality of teeth 521 arranged in fan-like configuration. Teeth 521 are used to clear bone material as will be later described. In a preferred embodiment, the front surface of rasp portion 520 is aligned along longitudinal axis 516. Front surface of rasp portion 520, and thereby longitudinal axis 516, are offset from the pair of parallel bores 505 and 506, and thereby from longitudinal axis 515, by angle D. Preferably angle D is substantially equivalent to angle A. As such, angle D may be any angle less than 90 degrees and is preferably in the range of about 30 degrees to about 75 degrees. As shown in FIG. 6, instrument 500 is cannulated having a bore 508 extending along longitudinal axis 510 of handle 502 from a first end 511 to a second end 512.

The fixation assembly 100 of the present invention is utilized to join two bones or two bone fragments together and to translate compression between the bones. FIGS. 7 and 8A-8F depict illustrative operative technique of an embodiment of the invention used joint a first bone (or bone fragment) 105 to a second bone (or bone fragment) 106. It will be understood that the operative technique is only illustrative, that the order of execution of some steps may vary, and that some steps may not need to be used in the treatment of a particular patient in accordance with the invention.

Figure 8A:
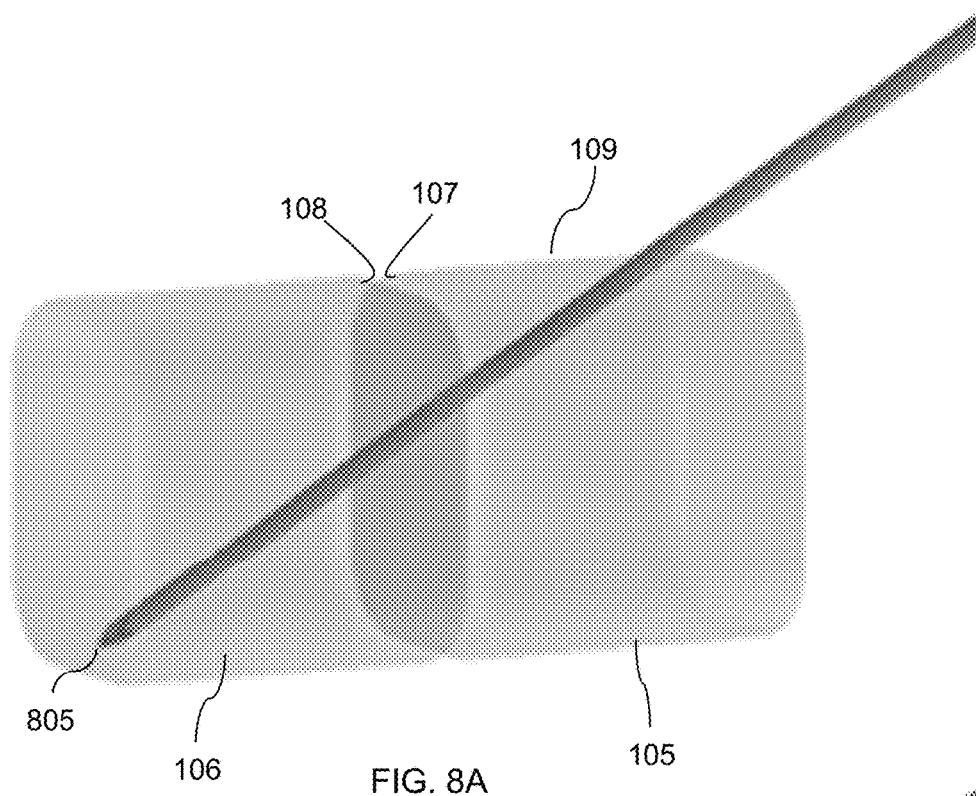
FIGS. 8A-8F depict details of certain steps of FIG. 7.
Figure 8B:
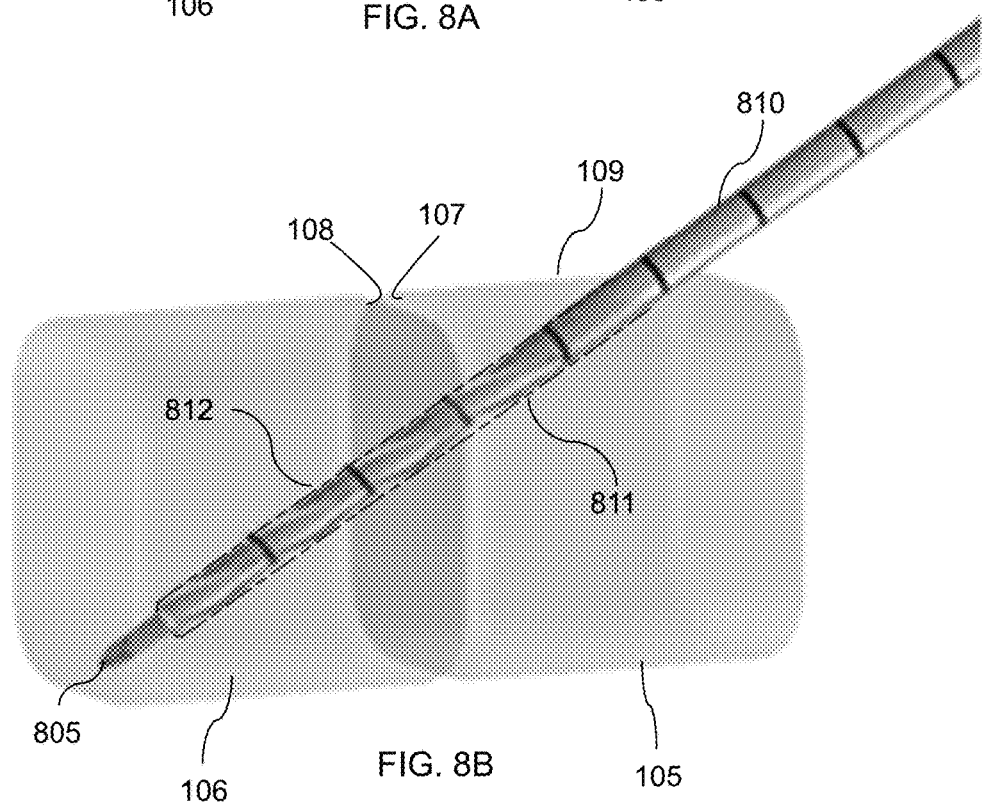

Initially, in step 710 an incision is made in the skin over first bone (or first bone fragment) 105 and second bone (or second bone fragment) 106. The incision may be a dorsal longitudinal incision or a two semi-elliptical incision. Next, in step 712 and as shown in FIG. 8A, a retrograde K-wire 805 is advanced diagonally into the side surface 109 of the first bone 105 and trough its proximal end 107. The K-wire 805 is further advanced through the distal end 108 of the second bone 106. The K-wire 805 is advanced by the surgeon in a direction of the desired alignment of the fixation assembly 100 with respect to the first and second bones 105 and 106. Then in step 714, as shown in FIG. 8B, the first and second bones 105 and 106 are drilled using drill bit 810 over the K-wire 805 to create a first hole 811 in the first bone 105 and a second hole 812 in the second bone 106. The K-wire 805 is used to guide drill bit 810 into the desired alignment. Accordingly, the drill bit 810 used in the present invention is preferably cannulated such that it may fit over the K-wire 805. The drill bit 810 may be driven manually or via a torque transmitting tool (not shown). Hole 811 extends from the side surface 109 to proximal end 107 of the first bone 105 and hole 812 extends through the distal end 108 into the second bone 106.

Figure 8C:
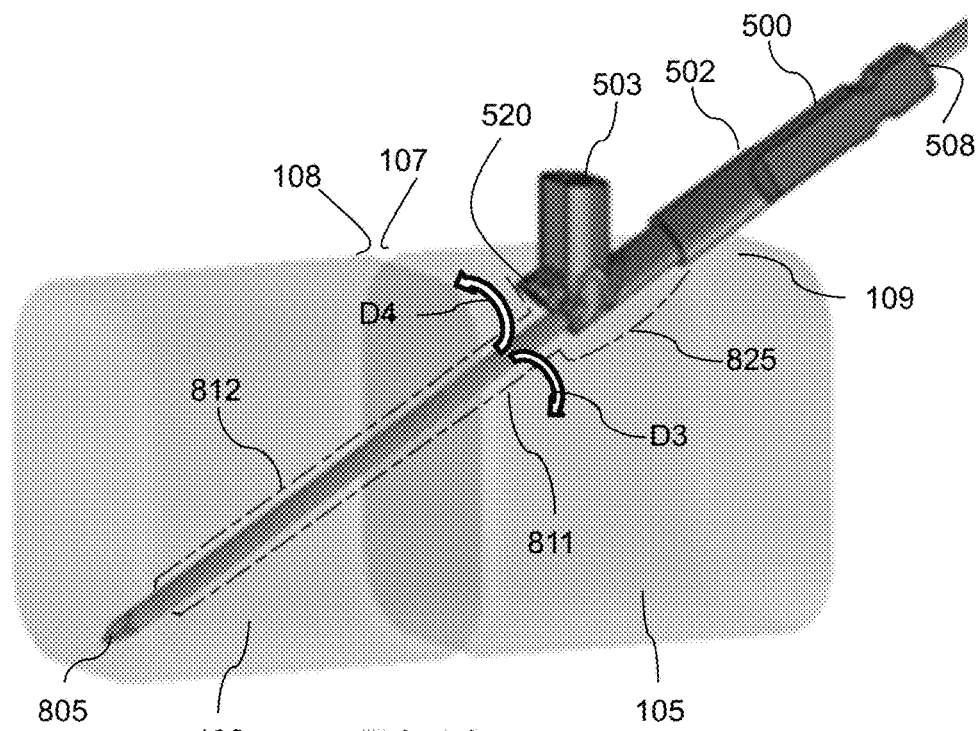

In step 716, as shown in FIG. 8C, instrument 500 is advanced over the K-wire 805 by inserting the K-wire 805 inside the bore 508 of instrument 500 until rasp portion 520 contacts the side surface 109 of first bone 105. Rasp portion 520 is used to remove bone material from side surface 109 to create a depression 825 in the side surface 109 of first bone 105 to fit the head portion 103 of post member 101. Since the longitudinal axis 516 of front surface of rasp portion 520 is offset from the longitudinal axis 515 of pair of parallel bores 505 and 506 by angle D (FIGS. 5A-5B), the depression 825 is angled to receive the head portion 103 in a flush configuration (FIG. 8E). In a preferred embodiment, the depression 825 is created deep enough in first bone 105 such that the head portion 103 sits within the depression 825 and is located below the side surface 109. The depth of depression 825 sets the depth the fixation assembly 100 is implanted into bones 105 and 106. To create depression 825, instrument 500 is partially rotated or wiggled back and forth in directions D3 and D4 by rotating handle 502 manually, or by connecting handle 502 to a torque transmitting tool (not shown). Rotating handle 502 rotates head portion 503 to scrape and remove bone material with teeth 521 of the rasp portion 520.

Figure 8D:
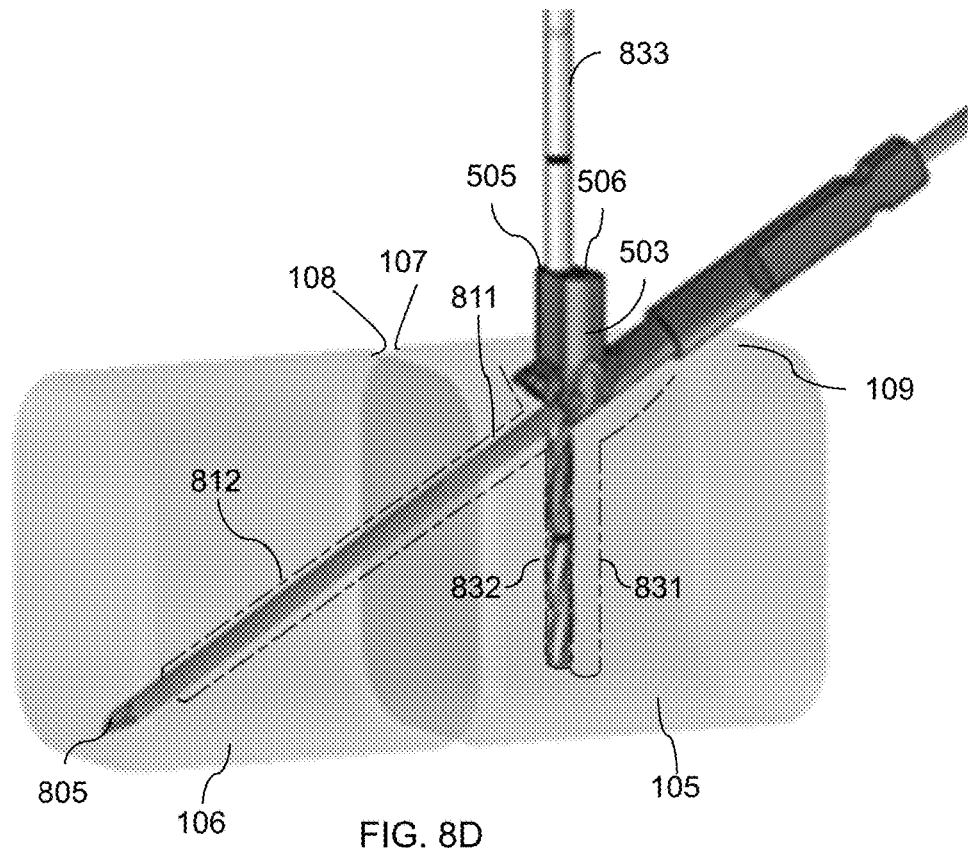
Figure 8E:
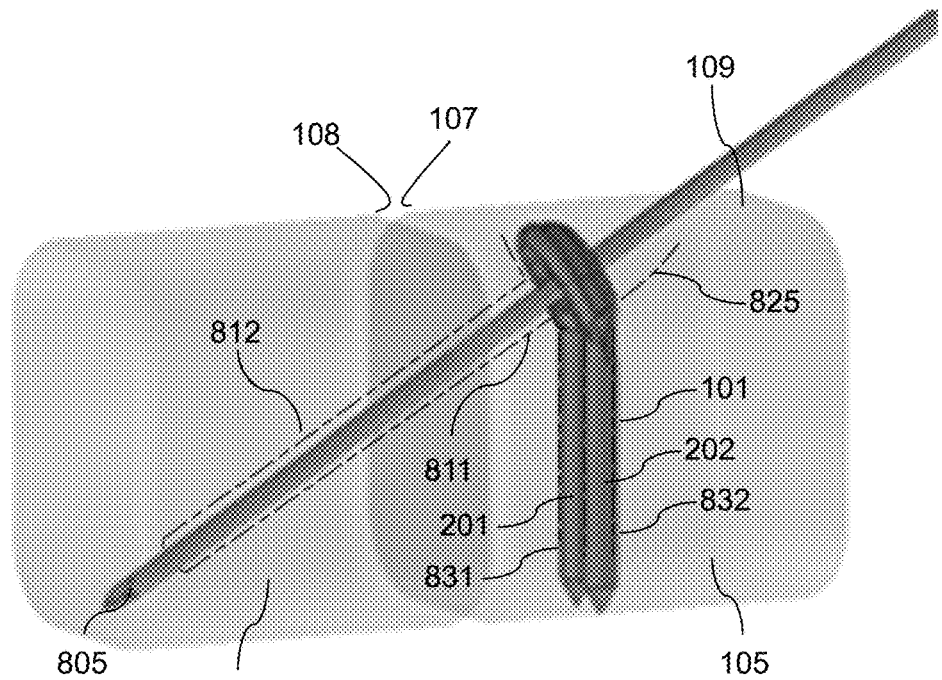

Next, in step 718, as shown in FIG. 8D, parallel bores 505 and 506 in head portion 503 of the instrument are used to align a drill bit 833 with first bone 105 to create third and fourth holes 831 and 832 in first bone 105. To create the holes, the head portion 503 is aligned with the first bone 105 and the drill bit 833 is inserted into each of the parallel bores 505 and 506 of head portion 503. In a preferred embodiment, third and fourth holes 831 and 832 are parallel and extend transversely with respect to first bone 105. After the third and fourth holes 831 and 832 are created, in step 720, first and second legs 201 and 202 are inserted into third and fourth holes 831 and 832, respectively, as shown in FIG. 8E. Head portion 103 is then pressed into the depression 825 until it is flush with the cortex of the bone. In alternative embodiments, post member 101 may be inserted by impaction, by press fit, by reaming, or substantially any other similar strategy or technique.

Figure 8F:
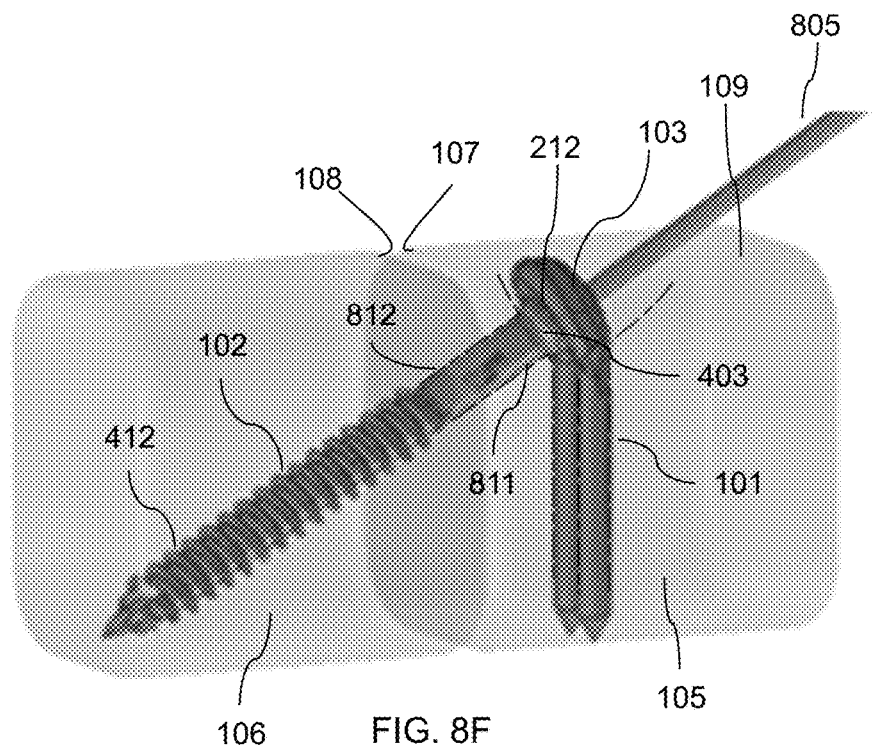

In step 722, the screw member 102 is advance over the K-wire 805, as shown in FIG. 8F, so that the K-wire guides the screw member 102 into first and second bones 105 and 106. Specifically, the K-wire 805 is inserted into bore 406 in the screw member 102, as shown in FIG. 8F. Screw member 102 is advanced through the bore 212 of the post member 101 and through first and second holes 811 and 812 in the first and second bones 105 and 106, respectively. Screw member 102 may be driven by inserting a torque transmitting tool into aperture 407 in the bulbous portion 403 and rotating the screw member 102, thereby engaging threads 412 with the second bore 812 in the second bone 106. Screw member 102 is rotatably advanced into the second bone 106 until the tapered bulbous portion 403 engages and locks with tapered bore 212 in head 103 of the post member 101. Finally, the K-wire 805 is removed from bones 105 and 106 and the incision is closed.

As will be apparent to those skilled in the art, numerous variations may be practiced within the spirit and scope of the present invention. For example, a variety of different tools—screw drivers, wrenches, reduction instruments and drill guides—may be used in the practice of the invention. Fixation assemblies of different sizes and different shapes may be used. Likewise, different thread sizes and configurations may be used. There may also be variation in the procedure used to implant the fixation assembly in the bones. Certain steps can be omitted or combined with other steps and certain steps can be performed in a different order. For example, in some procedures it may not be necessary to use a K-wire or pre-drill holes in the bones.

While the invention has been described with reference to the preferred embodiment and alternative embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the invention is capable of being embodied in other forms without departing from its essential characteristics.

The invention claimed is:

1. A fixation assembly for bone fixation, comprising:
a post member comprising an elongated body extending from a first end to a second end, wherein the post member comprises a head portion at the first end and an anchoring portion at the second end, wherein the anchoring portion comprises a first leg and a second leg extending from the head portion, wherein the first leg and second leg are each substantially straight and substantially parallel to each other and to a first longitudinal axis, wherein the head portion extends along a second longitudinal axis and comprises an annular bore, wherein the first longitudinal axis and the second longitudinal axis define a first angle, wherein the head portion comprises a partial ring annularly extending from a first end to a second end, and wherein the first leg extends from the first end of the partial ring and the second leg extends from the second end of the partial ring; and
a screw member extending from a first end to a second end along a third longitudinal axis, wherein the screw member couples to the post member such that the first and the third longitudinal axes define a second angle.

2. The fixation assembly of claim 1, wherein the screw member couples to the post member by inserting the screw member into the bore of the post member until the bulbous portion of the screw member abuts the bore of the post member.

3. The fixation assembly of claim 1, wherein the bore of the post member extends annularly from a first end to a second end, wherein the first end of the bore is separated from the second end of the bore by a slot.

4. The fixation assembly of claim 1, wherein at least one of the first angle and the second angle is less than 90 degrees.

5. The fixation assembly of claim 1, wherein the first angle is in the range of about 30 degrees to about 75 degrees.

6. The fixation assembly of claim 1, wherein the first angle determines the second angle of fixation of the post member with respect to the screw member.

7. The fixation assembly of claim 1, wherein the second angle is in the range of about 15 degrees to about 60 degrees.

8. The fixation assembly of claim 1, wherein the fixation assembly is capable of translating uniform compression to first and second bones or first and second bone fragments.

9. The fixation assembly of claim 1, wherein at least one of the post member and the screw member comprises a unitary elongated body.

10. The fixation assembly of claim 1, wherein at least one of the post member and the screw member comprises material selected from the group consisting of titanium, titanium alloy, stainless steel, cobalt chrome, PEEK, resorbable polyactic acid, osteoconductive material, plasma spray, and any combination thereof.

11. The fixation assembly of claim 1, wherein at least one of the bore of the post member and the bulbous portion comprises a taper for providing an interference fit.

12. The fixation assembly of claim 11, wherein the taper comprises a Morse taper.

13. The fixation assembly of claim 1, wherein the bore of the post member traverses the head portion through a width of the head portion and extends from a front face to a rear face of the head portion.

14. The fixation assembly of claim 1, wherein the anchoring portion is capable of being fixed transversely to a bone or a bone fragment.

15. The fixation assembly of claim 1, wherein the screw member is capable of being fixed diagonally to first and second bones or to first and second bone fragments.

16. The fixation assembly of claim 1, wherein the first and second legs are substantially cylindrical in shape.

17. The fixation assembly of claim 1, wherein each of the first and second legs comprises a rectangular cross-section or a semi-circular cross-section.

18. The fixation assembly of claim 1, wherein the first leg terminates at a first tip and wherein the second leg terminates at a second tip.

19. The fixation assembly of claim 18, wherein each of the first and second tips comprises a conical shape.

20. The fixation assembly of claim 18, wherein each of the first and second tips is tapered and terminates at a point.

21. The fixation assembly of claim 1, wherein the first and second legs comprise partially-flat front-facing surfaces, oppositely disposed partially-flat rear-facing surfaces, flat outer-facing surfaces, and curved inner-facing surfaces.

22. The fixation assembly of claim 21, wherein the first leg comprises a first tip and wherein the second leg comprises a second tip, wherein the first and second tips taper from the oppositely disposed flat outer facing surfaces to the curved inner facing surfaces.

23. The fixation assembly of claim 1, wherein the first leg comprises a first plurality of barbs extending transversely from the first leg and the second leg comprises a second plurality of barbs extending transversely from the second leg.

24. The fixation assembly of claim 23, wherein the first and second plurality of barbs buttress the first and second legs against a bone.

25. The fixation assembly of claim 1, wherein the elongated portion of the screw member is substantially cylindrical in shape.

26. The fixation assembly of claim 1, wherein the elongated portion of the screw member comprises a substantially uniform diameter.

27. The fixation assembly of claim 1, wherein the elongated portion of the screw member tapers from the bulbous portion to the second end of the screw member.

28. The fixation assembly of claim 1, wherein the elongated portion of the screw member comprises threads.

29. The fixation assembly of claim 1, wherein the screw member comprises a self-tapping leading edge at the second end of the screw member for removing bone material during insertion of the screw member into bone.

30. The fixation assembly of claim 1, wherein bulbous portion comprises an aperture for receiving a torque transmitting tool, wherein the aperture comprises a hexagonal-shaped aperture, a star-shaped aperture, or a square-shaped aperture.

31. The fixation assembly of claim 1, wherein the screw member is cannulated for receiving a guide wire.

32. The fixation assembly of claim 1, wherein the fixation assembly is capable of being coupled to bones or bone fragments using an instrument, wherein the instrument has an elongated body comprising:
a handle portion extending from a first end to a second end along a fourth longitudinal axis; and
a head portion connected to the first end of the handle portion and extending along a fifth longitudinal axis, wherein the fourth longitudinal axis and the fifth longitudinal axis define a third angle, wherein the head portion comprises a pair of parallel bores that traverse the head portion along the fifth longitudinal axis, wherein the first and second bores are used to guide a drill to create holes in a bone for receipt of the first and second legs of the post member.

33. The fixation assembly of claim 32, wherein the handle portion is ribbed, comprises a friction resistant material, or is sized to receive a torque transmitting tool.

34. The fixation assembly of claim 32, wherein the third angle is substantially equivalent to the second angle.

35. The fixation assembly of claim 32, wherein the head portion comprises an oval cross-section.

36. The fixation assembly of claim 32, wherein the head portion comprises a rasp portion for removing bone material to create a depression in a bone for receipt of the head portion of the post member.

37. The fixation assembly of claim 36, wherein the rasp portion comprises a plurality of teeth.

38. The fixation assembly of claim 37, wherein the plurality of teeth are arranged in a fan-like configuration.

39. The fixation assembly of claim 1, wherein the fixation assembly is capable of being implanted below the cortex of a bone.

40. A fixation assembly comprising:
a post member comprising a head portion connected to an anchoring portion, wherein the head portion is joined to the anchoring portion at a first angle, wherein the head portion comprises a curved body annularly extending from a first end to a second end, wherein the first end is separated from the second end by a slot, wherein the curved body defines an annular bore therein, wherein the anchoring portion comprises a first leg extending from the first end of the curved body at the first angle, and a second leg extending from the second end of the curved body at the first angle; and
a screw member comprising an elongated portion connected to a bulbous portion that couples with the bore of the post member.

* * * * *